(12) United States Patent
Lee et al.

(10) Patent No.: US 11,051,964 B1
(45) Date of Patent: Jul. 6, 2021

(54) POSTURE SUPPORTIVE BRA GARMENT WITH COMPRESSION PANELS

(71) Applicants: Vivian Jiyun Lee, Dublin, CA (US); Michelle Marie Rose, Oakland, CA (US)

(72) Inventors: Vivian Jiyun Lee, Dublin, CA (US); Michelle Marie Rose, Oakland, CA (US)

( * ) Notice: Subject to any disclaimer, the term of this patent is extended or adjusted under 35 U.S.C. 154(b) by 56 days.

(21) Appl. No.: 16/513,905

(22) Filed: Jul. 17, 2019

Related U.S. Application Data

(60) Provisional application No. 62/782,633, filed on Dec. 20, 2018.

(51) Int. Cl.
*A61F 5/02* (2006.01)
*A41C 3/00* (2006.01)

(52) U.S. Cl.
CPC ............. *A61F 5/026* (2013.01); *A41C 3/005* (2013.01); *A41C 3/0064* (2013.01); *A41C 3/0021* (2013.01)

(58) Field of Classification Search
CPC ... A41C 3/0057; A41C 3/0064; A41C 3/0021; A41C 3/005; A61F 5/026
USPC .......................... 450/2, 86, 19, 59, 74, 75, 76
See application file for complete search history.

(56) References Cited

U.S. PATENT DOCUMENTS

| | | | | | |
|---|---|---|---|---|---|
| 2,100,890 A | * | 11/1937 | Witkower | ................ | A41C 3/00 450/62 |
| 2,149,819 A | * | 3/1939 | Rubinstein | ............... | A41C 3/00 450/63 |
| 2,362,974 A | * | 11/1944 | Cohen | ................... | A41C 3/0021 450/59 |
| 2,400,499 A | * | 5/1946 | Gerace | ................. | A41C 3/0021 450/63 |
| 2,437,655 A | * | 3/1948 | Rosner | ................. | F02B 75/246 450/60 |
| 2,540,631 A | * | 2/1951 | Nelson | ..................... | A41C 3/10 450/55 |
| 2,553,225 A | * | 5/1951 | Weaver | ................ | A41C 3/0021 450/59 |
| 2,560,706 A | * | 7/1951 | Spetalnik | ............. | A41C 3/0021 450/74 |
| 2,591,462 A | * | 4/1952 | Mungo | ..................... | A41C 3/00 450/2 |
| 2,607,038 A | * | 8/1952 | Spare | .................... | A41C 3/0021 450/59 |
| 2,764,760 A | * | 10/1956 | Kaufman | ............ | A41C 3/0028 450/65 |
| 2,842,137 A | * | 7/1958 | Becker | ................. | A41C 3/0021 450/36 |

(Continued)

*Primary Examiner* — Jocelyn Bravo
(74) *Attorney, Agent, or Firm* — Plager Schack LLP; Mark H. Plager; Kara Verryt

(57) ABSTRACT

A posture supportive garment for supporting for a user's chest, back, and shoulders, while simultaneously reinforcing body alignment in the thoracic region to improve posture may include a bra structure having right and left cups sized to accommodate a user's breasts; a support base sized to encircle a user's torso, the support base attached to a bottom portion of the right and left cups; and right and left shoulder straps ultimately attached to the right and left cups, respectively, and the support base, wherein each of the right and left cups includes a compression sling; each of the right and left shoulder straps includes a lined compression panel; and the support base is made of a compression material.

6 Claims, 4 Drawing Sheets

(56) References Cited

U.S. PATENT DOCUMENTS

| | | | |
|---|---|---|---|
| 2,912,985 A * | 11/1959 | Plehn | A41C 3/00 450/65 |
| 3,036,575 A * | 5/1962 | Morehouse | A41C 3/00 450/65 |
| 3,067,751 A * | 12/1962 | Steiner | A41C 3/00 450/65 |
| 3,353,540 A * | 11/1967 | Erteszek | A41C 3/00 450/65 |
| 3,396,729 A * | 8/1968 | Glick | A41C 3/142 450/65 |
| 4,530,361 A * | 7/1985 | Wooten | A41C 3/0028 450/59 |
| 4,698,847 A * | 10/1987 | Yoshihara | A41D 13/0017 2/69 |
| 5,116,278 A * | 5/1992 | Sroub | A41C 3/14 2/67 |
| 5,221,227 A * | 6/1993 | Michels | A41C 3/0057 2/73 |
| 5,643,043 A * | 7/1997 | Pflum | A41C 3/0057 2/73 |
| 5,660,577 A * | 8/1997 | Modena | A41C 3/00 450/86 |
| 5,823,851 A * | 10/1998 | Dicker | A41C 3/0057 450/2 |
| 5,863,236 A * | 1/1999 | Johnson | A41C 3/0057 450/60 |
| 6,023,785 A * | 2/2000 | Johnson | A41C 3/0057 2/62 |
| 6,387,067 B1 * | 5/2002 | Hebert | A61F 5/026 2/44 |
| 6,855,029 B2 * | 2/2005 | Rothman | A41C 3/04 450/36 |
| 7,435,155 B2 * | 10/2008 | Reinisch | A41C 3/0028 450/59 |
| 7,909,675 B1 * | 3/2011 | Rainey | A41C 3/148 450/59 |
| 8,047,893 B2 * | 11/2011 | Fenske | A41C 3/005 450/86 |
| 8,128,457 B2 * | 3/2012 | Reinisch | A41C 3/0057 450/59 |
| 8,241,089 B2 * | 8/2012 | Otto | A41C 3/00 450/86 |
| 8,523,629 B2 * | 9/2013 | Pundyk | A41C 3/0021 450/36 |
| 8,900,032 B2 * | 12/2014 | Punsal | A41C 3/122 450/31 |
| 8,932,103 B2 * | 1/2015 | Hansen | A41C 3/0028 450/59 |
| 9,192,197 B2 * | 11/2015 | Reinhard | A41C 3/02 |
| 9,480,287 B2 * | 11/2016 | Black | A41F 15/007 |
| 9,795,172 B1 * | 10/2017 | Lee | A41C 3/0021 |
| 9,839,242 B2 * | 12/2017 | Yuasa | A41C 3/128 |
| 10,485,270 B2 * | 11/2019 | Wesley | A41C 3/12 |
| 10,595,568 B2 * | 3/2020 | Parkinson | A41C 3/12 |
| 2001/0019933 A1 * | 9/2001 | Wagner | A41C 3/02 450/37 |
| 2004/0133959 A1 * | 7/2004 | Horii | A41D 7/00 2/69 |
| 2006/0025039 A1 * | 2/2006 | Barbour | A41D 1/18 450/1 |
| 2006/0252346 A1 * | 11/2006 | Reinisch | A41C 3/0028 450/86 |
| 2007/0016120 A1 * | 1/2007 | Latronica | A61F 5/026 602/19 |
| 2008/0026676 A1 * | 1/2008 | Rothman | A41C 3/08 450/36 |
| 2009/0098803 A1 * | 4/2009 | Reinisch | A41C 3/0014 450/39 |
| 2009/0265831 A1 * | 10/2009 | Hendrickson | A41D 1/215 2/104 |
| 2010/0005569 A1 * | 1/2010 | Sanders | A41C 3/0057 2/400 |
| 2011/0214216 A1 * | 9/2011 | Zarabi | A41D 1/00 2/69 |
| 2011/0275278 A1 * | 11/2011 | Shashy | A41C 3/0057 450/86 |
| 2012/0122370 A1 * | 5/2012 | Heath | A41C 3/0057 450/80 |
| 2012/0142252 A1 * | 6/2012 | Hopkins | A41D 31/12 450/31 |
| 2012/0244782 A1 * | 9/2012 | Pundyk | A41C 3/0057 450/70 |
| 2014/0017977 A1 * | 1/2014 | Horii | A41C 3/0014 450/31 |
| 2014/0087624 A1 * | 3/2014 | Yuasa | A41C 3/12 450/1 |
| 2015/0056890 A1 * | 2/2015 | Black | A41F 15/007 450/86 |
| 2015/0080860 A1 * | 3/2015 | Farrell | A41C 3/0064 604/540 |
| 2016/0015090 A1 * | 1/2016 | Mazourik | A41C 3/0071 450/39 |
| 2017/0273365 A1 * | 9/2017 | Muhlenfeld | A41C 3/12 |
| 2018/0085620 A1 * | 3/2018 | Feldman | A63B 21/4007 |
| 2018/0343929 A1 * | 12/2018 | Parkinson | A41C 3/12 |
| 2019/0261696 A1 * | 8/2019 | Hirakubo | A41C 3/0021 |
| 2019/0297958 A1 * | 10/2019 | Liu | A41F 15/00 |
| 2019/0297959 A1 * | 10/2019 | Liu | A41C 3/0064 |
| 2020/0008496 A1 * | 1/2020 | Liu | A41C 3/0064 |
| 2020/0253291 A1 * | 8/2020 | Liu | A41F 15/00 |

* cited by examiner

POSTURE SUPPORTIVE BRA GARMENT WITH COMPRESSION PANELS

RELATED APPLICATION

This application claims priority to provisional patent application U.S. Ser. No. 62/782,633 filed on Dec. 20, 2018, the entire contents of which is herein incorporated by reference.

BACKGROUND

The embodiments herein relate generally to garments, and more particularly, to a posture supportive bra with strategically placed compression panels to provide not only support for a user's chest, back, and shoulders, but also to improve a wearer's posture.

Posture refers to the alignment of the body while standing, sitting, or lying down. Poor posture is cited as a common cause of chronic issues, including tension headaches, and back, shoulder, and neck pain. Moreover, poor alignment can lead to spinal distortions over time. Additionally, sources have cited that up to 80% of women are wearing ill-fitting bras, which place increased pressure on the bra wearer's back, shoulder blades, and neck muscles to overcompensate for the lack of structural support for the breasts, shoulders, and back.

Therefore, what is needed is a posture supportive garment that includes a well-integrated system of sensory compression that supports the weight of breasts and redistributes weight to the shoulders, wherein the design reinforces a better postural stance by applying supportive compression in the thoracic region of the back, shoulders, and chest.

SUMMARY

Some embodiments of the present disclosure include a posture supportive garment for supporting for a user's chest, back, and shoulders, while simultaneously reinforcing body alignment in the thoracic region to improve posture. The garment may include a bra structure having right and left cups sized to accommodate a user's breasts; a support base sized to encircle a user's torso, the support base attached to a bottom portion of the right and left cups; and right and left shoulder straps ultimately attached to the right and left cups, respectively, and the support base, wherein each of the right and left cups includes a compression sling; each of the right and left shoulder straps includes a compression panel; and the support base is made of a compression material.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
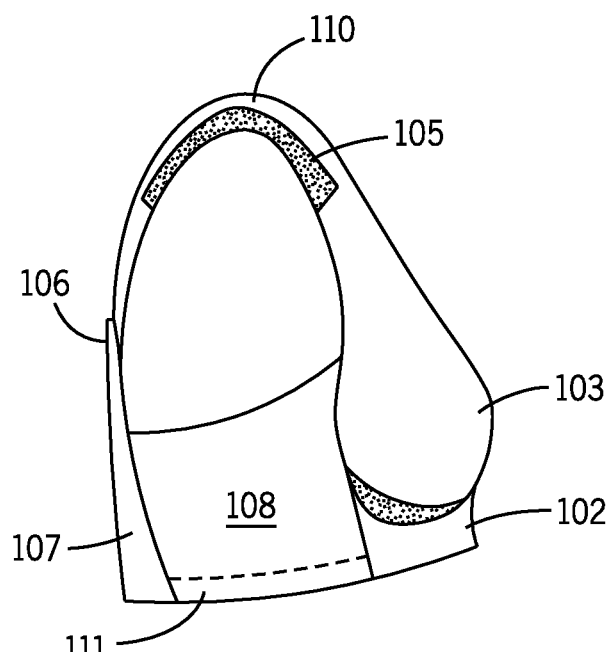
FIG. 1 is a side perspective view of one embodiment of the present disclosure.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a posture supportive garment and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

a. Garment
b. Compression Panels

The various elements of the device of the present disclosure may be related in the following exemplary fashion. It is not intended to limit the scope or nature of the relationships between the various elements and the following examples are presented as illustrative examples only.

By way of example, and referring to FIGS. 1-6, some embodiments of the present disclosure include a posture supportive garment for supporting for a user's chest, back, and shoulders, while simultaneously reinforcing body alignment in the thoracic region to improve posture, wherein the garment may comprise a bra structure, including cups 103a, 103b, shoulder straps 110a, 110b, and a support base encircling the user's torso, the cups 103a, 103b and shoulder straps 110a, 110b ultimately attaching to the support base, wherein the cups 103a, 103b, shoulder straps 110a, 110b, and support base 102 each comprise compression materials.

In a particular embodiment, the garment may comprise a right cup 103a and a left cup 103b, wherein each of the cups 103a, 103b is sized to accommodate a user's breasts, a right shoulder strap 110a extending from the right cup 103a and coupled to an upper back panel 109, specifically a right upper back panel 109a, and a main back panel 107, such as a right main back panel, a left shoulder strap 110b extending from the left cup 103b and coupled to a left upper back panel 109b and a main back panel 107, such as a left main back panel, a support base 102 extending along a bottom edge of the right cup 103a and the left cup 103b and between the right cup 103a and the left cup 103b, the support base 102 having a size sufficient for extending along a width of a front surface of the user's torso, side panels 108 such as a right side panel and a left side panel, attaching each of the cups 103a, 103b to the respective main back panel 107, and a thoracic spine panel 106 positioned between the right upper panel and the left upper back panel and between the right main back panel and the left main back panel, the thoracic spine panel extending from a top periphery to a bottom periphery along a central portion of a back of the garment, the thoracic spine panel 106 extending an entire height of the back panels 107, 109, wherein the support base 102 and the thoracic spine panel 106 each comprise a compression material, a bottom portion of each cup 103a, 103b comprises an encapsulating compression sling 114a, 114b, the shoulder straps 110 each comprise an outer compression strap panel 105a, 105b positioned on an outer edge thereof, and each of the side panels 108 include a side compression panel 115 incorporated therein. As shown in the Figures, the right main back panel may extend from a right edge of the thoracic spine panel 106 to a rearmost edge of the right side panel; the right main back panel may extend continuously downward from the right shoulder strap 110a to the support base 102; the left main back panel may extend from a left edge of the thoracic spine panel 106 to a rearmost edge of the left side panel; and the left main back panel may extend continuously downward from the left shoulder strap 110b to the support base 102. In some embodiments, the garment may further comprise a lower elastic edge 111 running along the bottom edge of the main back panel 107 and the side panels 108 and connecting to both edges 102c of the support base 102. The lower elastic edge 111 may help keep the garment more firmly in place, preventing the garment from riding in any direction. In embodiments, the garment may resemble a sports bra or compression top. However, the garment with the compression panels may be incorporated into any desired upper body garment including tops, shirts, sweaters, camisoles, and the like.

Figure 2:
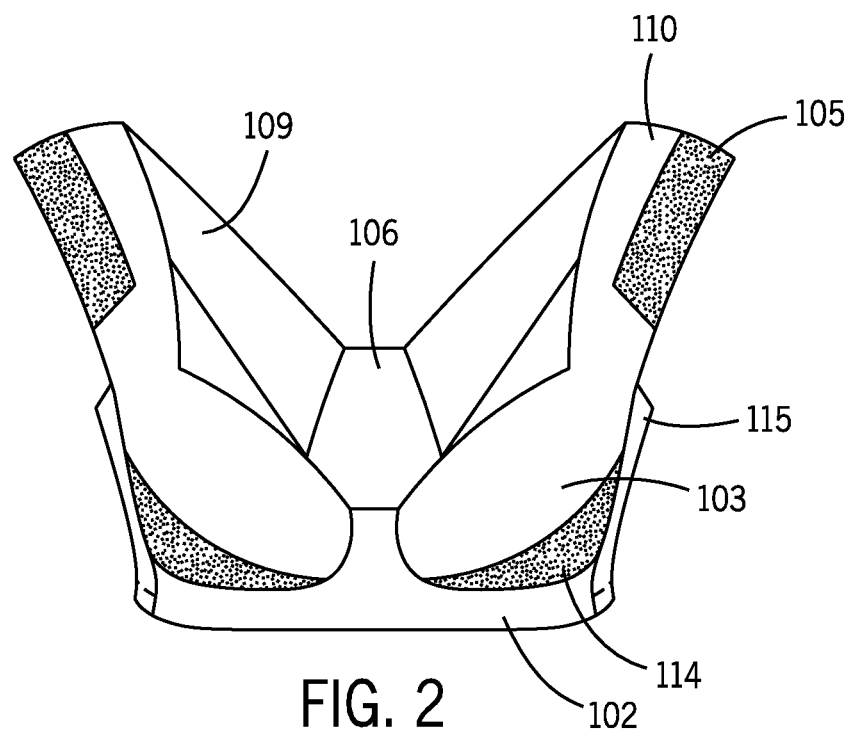
FIG. 2 is a front perspective view of one embodiment of the present disclosure.
Figure 4:
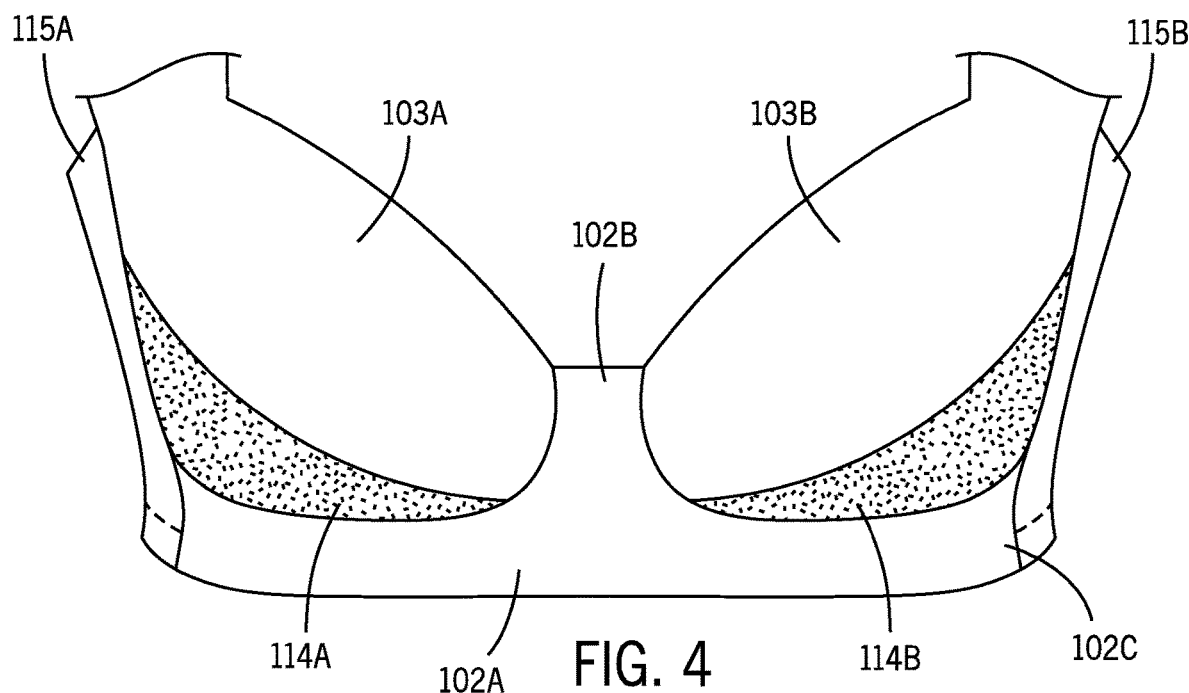
FIG. 4 is a front perspective view of one embodiment of the present disclosure.
Figure 5:
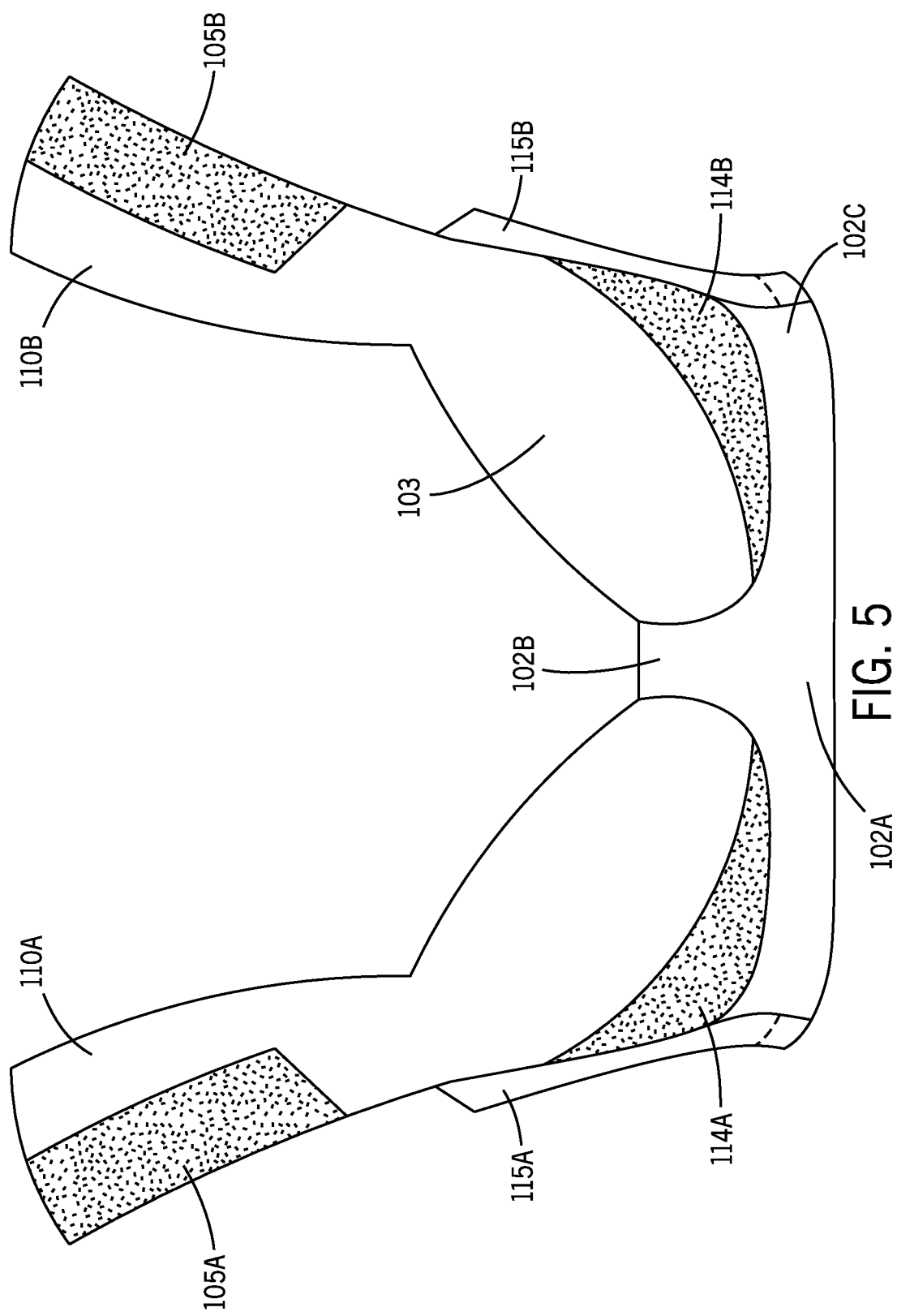
FIG. 5 is a partial front perspective view of one embodiment of the present disclosure.
Figure 6:
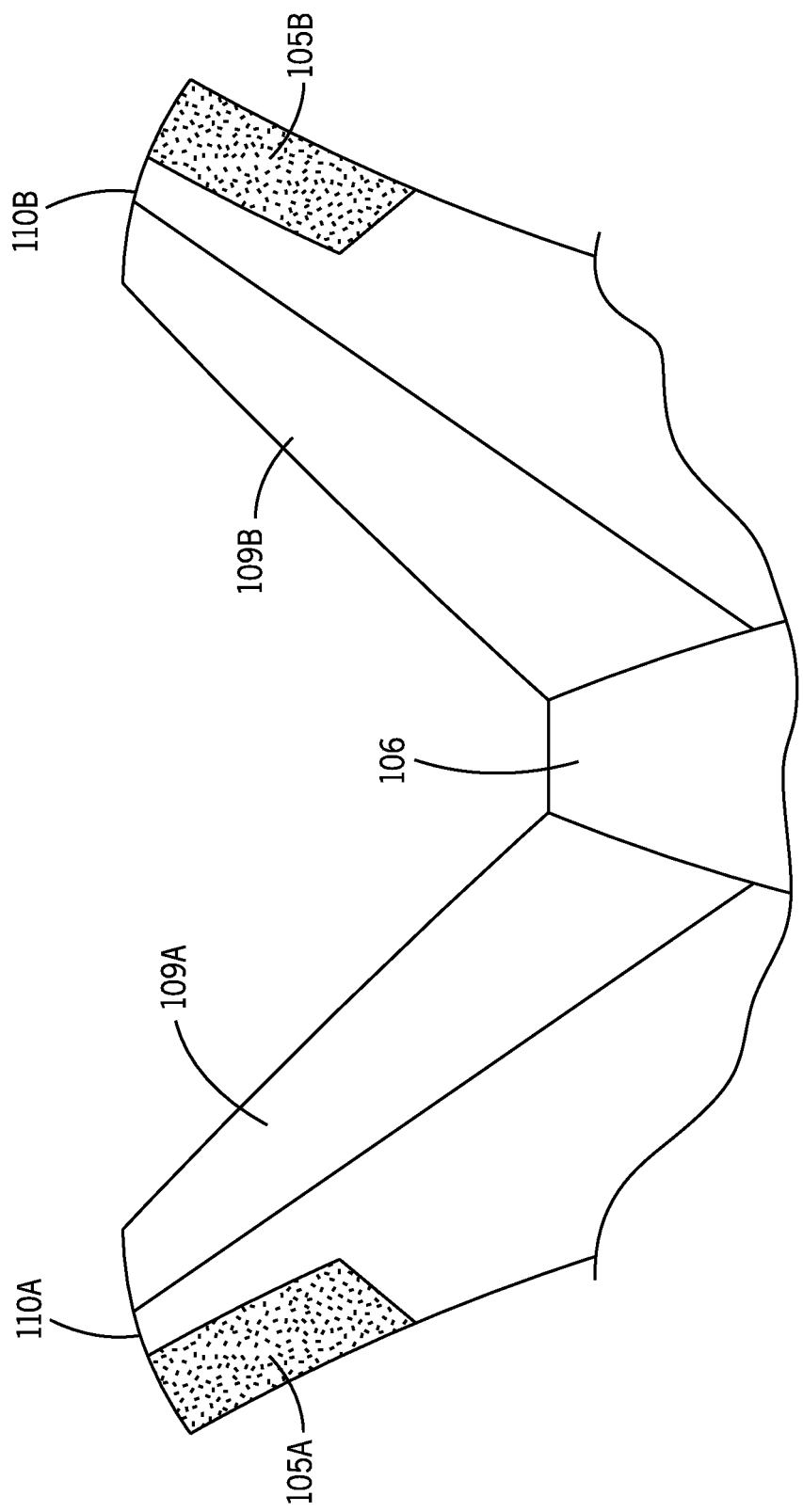
FIG. 6 is a partial front perspective view of one embodiment of the present disclosure.

As shown in FIGS. 1, 2, and 4, the support base 102 may comprise a breast support structure comprising an elongate portion 102a extending from an outer side of the right breast to an outer side of the left breast, thus extending the entire width of the user's torso. A center point separation portion 102b may extend upwards from the elongate portion 102a between the breasts and, thus, between cups 103a and 103b, helping to lift and separate the breasts. The outer edges 102c of the elongate portion 102a may provide additional side support to each breast. In addition, as mentioned above, each cup 103 may include an encapsulated sling 114, which may help effectively lift each individual breast by creating a sling-like bridge that extends from an outer edge of each cup and attaches to the center point separation portions 102b, stabilizing the encapsulated sling 114. Lastly, side support may be reinforced with side compression panels 115a, 115b, wherein the side compression panels 115 may be built into each side panel 108. The interaction of the above described components may provide a structure that creates encapsulation, lift, and separation of the breasts.

As described above, each shoulder strap 110 may include a shoulder strap compression panel 105. Each shoulder strap compression panel 105 may be positioned to encapsulate each shoulder and apply a compression force across the end of each shoulder blade. These compression panels 105 may shift pressure away from the midpoint of the shoulder blades, thereby redistributing the weight of the breast across the widest part of the shoulders, reducing stress on the shoulders, and also encouraging the user to roll back her shoulders. Moreover, the shoulder straps 110 with the incorporated compression panels 105 may reduce the possibility of the shoulder straps 110 from slipping off of the user's shoulders during use. In a particular embodiment, each of the shoulder straps 110 may include adhesive bonding in the lining thereof, wherein the adhesive bonding may grip the shoulders, encourage the user to roll back her shoulder, and help prevent the shoulder strap from slipping or otherwise falling off of the user's shoulder.

Figure 3:
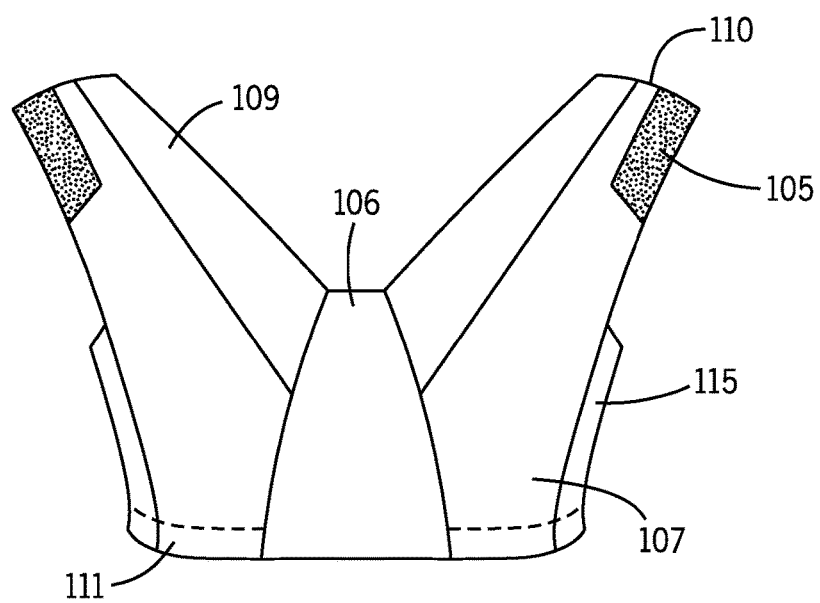
FIG. 3 is a rear perspective view of one embodiment of the present disclosure.

As shown in, for example, FIG. 3, each of the shoulder straps 110 may ultimately attach to the thoracic spine compression panel 106. This may further balance the redistribution of the weight of the breasts, thus anchoring support in the back and reinforcing the widest part of the back with upper back panels 109. These upper back panels 109 may extend at slight diagonal angles from the shoulders toward the center, thoracic portion of the back. The neckline of the garment may vary depending on the desires of the user, as long as the compression forces are centered in the areas of the upper back panels 109 and the thoracic panel 106.

The garment of the present disclosure may be made of any desired materials. In embodiments, the various compression panels may comprise any suitable compression material, wherein the compression panels may be built into the interior portion of the garment such that they are not necessarily perceived visually from the outside of the garment. However, this is not a requirement. The compression materials may comprise synthetic elastic materials, such as polyester, nylon spandex, elastane, or the like, wherein the material may provide different levels of stretch and compression, with the higher levels of compression being positioned in the areas of the shoulders and back (i.e., in the various compression panels). In a particular embodiment, the upper back panels 109a, 109b may be lined with a high compression synthetic material, such as a mesh fabric comprising nylon spandex, to create higher levels of targets compression along the upper back, working in concert with the shoulder straps to reinforce better postural stance. However, the use of other suitable materials is envisioned. The materials used to make the garment of the present disclosure may also be antimicrobial with built-in UPF50 UV protection, machine washable, and moisture wicking.

While the basic structure of the garment is described above, additional components may be added, as desired. For example, additional seaming may be added to the encapsulation area of the breasts to achieve various desired cup shapes and sizes. Moreover, bra pad inserts may be inserted as removable, or as permanent implementations, to produce the desired shaping of the breasts while reducing gaping in the bust area.

Because of the positioning of the compression panels, the garment of the present disclosure may provide an integrated system of support for the breasts, shoulders, and back. The system of support throughout the thoracic region may work in unison to promote and encourage better body alignment and improved postural stance. Due to the three-dimensional structure of the garment of the present disclosure, using the garment may provide cushioned compression that lifts and elevates the bust, shoulders, and back. The shoulder straps, optionally being wider than conventional shoulder straps, may reduce pressure on the user's shoulder blades.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A posture supportive garment for supporting a user's chest, back, and shoulders, while simultaneously reinforcing body alignment in a thoracic region of the user to improve posture, the garment comprising:
    a right cup and a left cup, wherein each of the cups is sized to accommodate one breast of the user;
    a right shoulder strap extending from the right cup and coupled to a right upper back panel and a right main back panel;
    a left shoulder strap extending from the left cup and coupled to a left upper back panel and a left main back panel;
    a support base extending along a bottom edge of the right cup and along a bottom edge of the left cup and extending between the right cup and the left cup, the support base configured to extend along a width of a front surface of a torso of the user;
a right side panel attaching the right cup to the right main back panel;
a left side panel attaching the left cup to the left main back panel; and
a thoracic spine panel positioned between the right upper panel and the left upper back panel and between the right main back panel and the left main back panel, the thoracic spine panel extending from a top periphery of the garment to a bottom periphery of the garment along a central portion of a back of the garment,
wherein:
- the right main back panel extends laterally from a right edge of the thoracic spine panel to a rearmost edge of the right side panel;
- the right main back panel extends continuously downward from the right shoulder strap to the bottom periphery of the garment;
- the left main back panel extends laterally from a left edge of the thoracic spine panel to a rearmost edge of the left side panel;
- the left main back panel extends continuously downward from the left shoulder strap to the bottom periphery of the garment;
- the support base and the thoracic spine panel each comprise a compression material;
- a bottom portion of each cup comprises an encapsulating compression sling;
- the shoulder straps each comprise a shoulder strap compression panel positioned on an outer edge of each shoulder strap; and
- each of the side panels includes a side compression panel incorporated within each side panel.

2. The posture supportive garment of claim 1, further comprising a lower elastic edge running along a bottom edge of each main back panel and along a bottom edge of each side panel and connecting to a left edge of the support base and to a right edge of the support base.

3. The posture supportive garment of claim 1, wherein the support base comprises a breast support structure comprising:
   an elongate portion extending from an outer side of the right cup to an outer side of the left cup; and
   a center point separation portion extending upwards from the elongate portion between the right cup and the left cup.

4. The posture supportive garment of claim 3, wherein each encapsulating compression sling comprises a sling-like bridge extending from a respective outer edge of each cup and attaching to and terminating at the center point separation portion.

5. The posture supportive garment of claim 1, wherein the shoulder strap compression panels are positioned and configured to encapsulate each of the user's shoulders and configured to apply a compression force across an end of each shoulder blade.

6. The posture supportive garment of claim 1, wherein each of the shoulder straps includes adhesive bonding in a lining of each shoulder strap.

* * * * *